United States Patent
Zimmermann

Patent Number: 5,290,267
Date of Patent: Mar. 1, 1994

[54] HYPODERMIC NEEDLE

[75] Inventor: Michael Zimmermann, St. Wendel, Fed. Rep. of Germany

[73] Assignee: Fresenius AG, Bad Homburg, Fed. Rep. of Germany

[21] Appl. No.: 20,887

[22] Filed: Feb. 19, 1993

Related U.S. Application Data

[63] Continuation of Ser. No. 822,498, Jan. 17, 1992, abandoned.

[30] Foreign Application Priority Data

Jan. 17, 1991 [DE] Fed. Rep. of Germany ....... 4101231

[51] Int. Cl.⁵ .............................................. A61M 5/00
[52] U.S. Cl. .................................... 604/272; 604/274
[58] Field of Search ............................... 604/272–274, 604/158, 164

[56] References Cited

U.S. PATENT DOCUMENTS

| | | | |
|---|---|---|---|
| 3,099,988 | 8/1963 | Ginsburg | 604/272 |
| 3,788,320 | 1/1974 | Dye | 604/272 X |
| 4,383,530 | 5/1983 | Bruno | 604/274 |
| 4,490,139 | 12/1984 | Huizenga et al. | 604/272 X |
| 4,565,545 | 1/1986 | Suzuki | 604/272 X |
| 4,889,529 | 12/1989 | Haindl | 604/274 |

FOREIGN PATENT DOCUMENTS

| | | |
|---|---|---|
| 0301246 | 1/1989 | European Pat. Off. |
| 2230632 | 1/1973 | Fed. Rep. of Germany |

*Primary Examiner*—John D. Yasko
*Attorney, Agent, or Firm*—Robbins, Berliner & Carson

[57] ABSTRACT

The invention concerns a cannula comprising a cannula tube with a preferably rigid upper section, an end section which is bent laterally and a hook-shaped curved section which has in its concave side a tangentially inward ground lumen opening. The lumen opening has a sharply inwardly directed rear edge. This results in the advantage that during piercing of natural and synthetic walls the cutting of plugs from the material to be perforated is avoided.

9 Claims, 2 Drawing Sheets

FIG. 1
FIG. 2
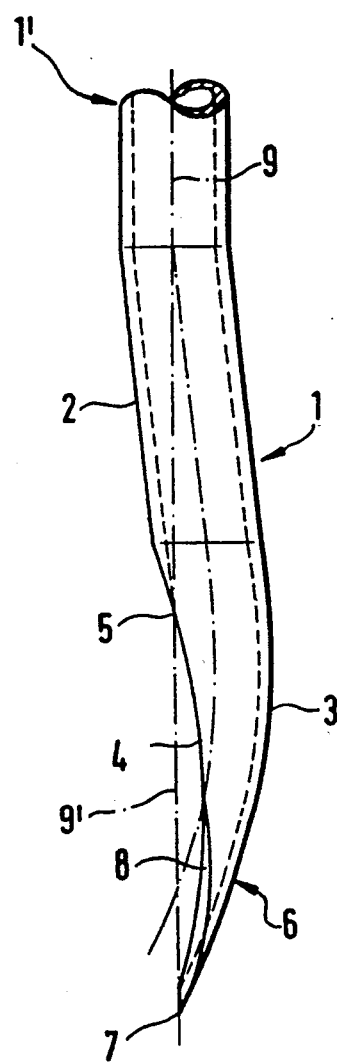
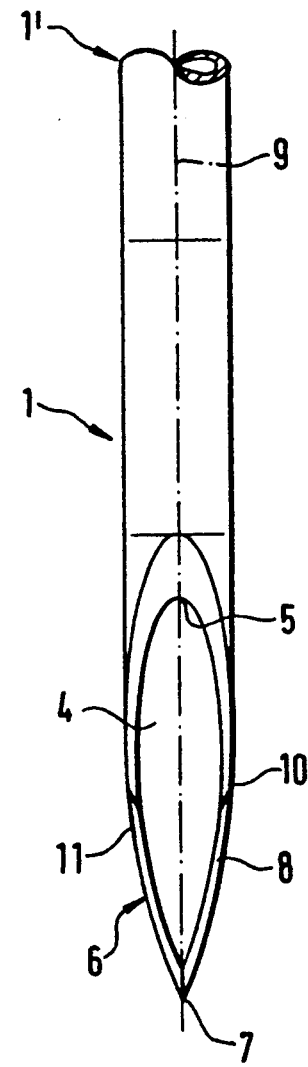

| Sharpening | | | |
|---|---|---|---|
| $\alpha = 6°$ | | | |
| $c = 1/3$ to $1/2$ $a$ | | | |
| Cannula $\phi$ d | a | b | r |
| 0,6 | 2,5 | 2,0 | 3,75 |
| 0,7 | 3,0 | 2,0 | 4,50 |
| 0,8 | 3,4 | 2,5 | 5,10 |
| 0,9 | 3,9 | 2,5 | 5,80 |
| 1,0 | 4,3 | 3,0 | 6,40 |
| 1,1 | 4,8 | 3,0 | 7,20 |
| 1,2 | 5,2 | 3,0 | 7,80 |
| 1,5 | 6,5 | 4,0 | 9,75 |

HYPODERMIC NEEDLE

This is a continuation of Ser. No. 07/822,498 filed Jan. 17, 1992, now abandoned.

BACKGROUND OF THE INVENTION

The invention relates to a cannula for use, for example, in the administration and removal of fluids.

Conventional piercing cannulae have as a piercing part a more or less sharply inclined wedge-shaped ground portion of the tube end, which in a top view appears as an oval lumen opening in line with the bore of the tube, with the rear edge of the lumen opening forming a cutter. The edges of the lower zone of the piercing part are usually ground into a point.

In piercing, such a tip on the piercing part results in the fact that the sharp rear cutter of the lumen opening cuts a plug of this material necessarily forced into it from the surface to be penetrated, consequently enlarging the pierced hole.

On the one hand, this is disadvantageous with tissue piercing because of the traumatization, and, on the other hand, the plug-cutting effect proves to be extremely undesirable when such cannulae are used to pierce implantable catheter ports. Such systems consist as a rule of an implanted capsule which has a hollow bore for removal or administration of a fluid such as blood, blood components, or a medicament. The capsule is connected with a cathether which opens into a vessel or other site of action. The wall of the capsule toward the skin of the patient consists of a pierceable elastomer membrane which is penetrated by the cannula through the skin.

The piercing of a cannula through the membrane of the capsule causes breaks in the seal because of the fact that the cutter at the rear edge of the lumen opening cuts out a plug of elastomer material, resulting in holes which no longer close automatically due to the elastic force of the material. This leads to the circumstance that the implanted capsule already has leaks after a few insertions. Furthermore, elastomer plugs can be carried by the flow into the patient or block the catheter.

Because of these problems, to date so-called Huber cannulae have been used to pierce such administrative arrangements. In a generic cannula, known from U.S. Pat. No. 2,748,769, the front end of the cannula tube is bent to the side at an angle such that the wedge-shaped ground end of the tube runs substantially parallel to the longitudinal axis of the tube, whereby plug cutting of membrane material is supposed to be avoided. In this embodiment, the lumen opening is significantly outside the line of the tube. This circumstance can lead to damage to the membrane even with proper, perpendicular insertion of the cannula, since the angled front section of the cannula tube penetrates the surface in the shape of a wedge and the diverted ground configuration parallel to the axis presses against the material to be penetrated, with this ground portion acting like a plane and slicing off material which is pressed against it.

Another embodiment of a Huber cannula is known from U.S. Pat. No. 2,409,979. The embodiment described has a straight cannula tube which opens into a lumen opening directed toward the side, which is shaped such that side of the cannula wall opposite the lumen opening is bent at an angle in the direction of the axis. The wall surrounding the lumen opening is ground even with the outside surface of the cannula tube and forms a cutter on the rear edge.

Because of the beveled surface of the cannula tube, this embodiment as well exhibits a wedge effect during piercing of a synthetic or natural wall such that the material forced into the lumen opening during thrusting of the cannula, favored by the cutter which angles slightly inward, is sliced off or damaged by pinching.

Another cannula is known wherein there is a needle whose front piercing part is designed in the shape of a hook, whereby during the piercing of a vein, for example, the danger of injury to the opposing wall of the vessel is supposed to be prevented.

The front, rounded edge of the piercing part lies in the line of the outside wall of the cannula tube. It has no flat ground edge, while the rear edge of the lumen opening is ground flat to form a cutter. The side of the tube opposite the lumen opening forms a sharply curved surface which acts as a slip surface. This shape forces an angular incidence during piercing, with the course of the pierce following an insertion path corresponding to the radius of curvature of the slip surface. With this procedure, material of the surface to be penetrated is of necessity forced into the lumen opening, which material is cut as a plug by the flat rear cutter, and thus the pierce hole is likewise enlarged.

Finally, additional cannulae are known from GB-A-2 073 026 and U.S. Pat. No. 2,717,599 which, however, present the same problems as the two cannulae described.

In contrast, the object of the present invention is to design a cannula of a type, such that plug cutting is avoided during the piercing of natural or synthetic walls.

SUMMARY OF THE INVENTION

In accordance with the present invention there is provided a cannula in which the cannula tube is angled to the side toward the piercing part and in its further course is designed in the shape of a hook and has a lumen opening tangentially ground into the concave shape of the tube which continues in the shape of a hook, which lumen opening has on its rear edge a sharply inward directed cutter resulting from the shape of the tube. Advantageously, the walls of the lumen opening form a lancet-shaped point with beveled ground surfaces, whereby the point of the piercing part is in line with the imaginary axis line of the otherwise straight cannula tube.

BRIEF DESCRIPTION OF THE DRAWINGS

The invention may be better understood with the references to the accompanying drawings, in which:

FIG. 1 represents a side view of an embodiment of a cannula according to the invention;

FIG. 2 represents a front view of the cannula according to FIG. 1; and

DETAILED DESCRIPTION OF THE INVENTION

Figures 3A, 3B:
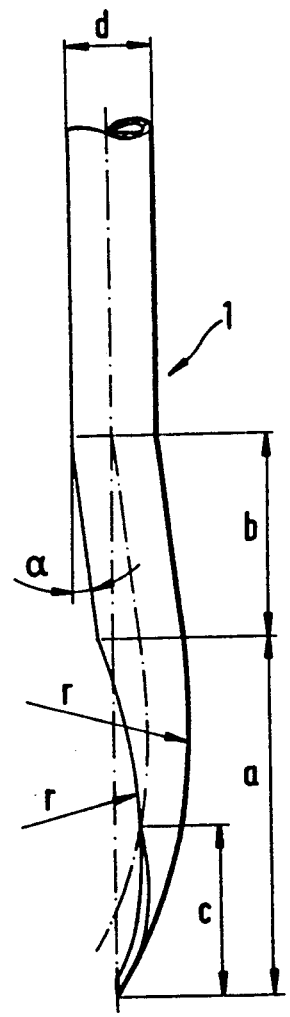
FIG. 3A, FIG. 3B illustrates dimensional parameters correlated with the individual parts of a cannula according to the basic design principles illustrated in FIGS. 1 and 2.

With the cannula according to the invention, a reduced plug cutting effect occurs during the piercing of synthetic or natural walls, since the sharply inward directed rear edge of the lumen opening works with the opposing cannula wall which is curved outward in the shape of a hook such that the insertion channel is widened by the rear and the cannula slides through the wall without a planing effect because of the inward directed rear edge of the ground opening. The cannula point, which is preferably in line with the imaginary axis line of the tube, further improves the reduction of the wedge effect and preferably reduces the danger of pressing material into the lumen opening, which in conjunction with the inward directed rear edge of the lumen opening additionally favors particularly advantageous plug- or slice-free piercing.

Thus, the cannula according to the invention is suitable for atraumatic piercing of natural tissues or synthetic membranes particularly when the cannulae have a large interior diameter because of the flow volume required.

FIGS. 1 and 2 depict an embodiment of a cannula 1 according to the invention which has a straight, preferably rigid upper section of cannula tube 1' (hereinafter, cannula tube 1') with a flow bore represented by broken lines.

The cannula 1 also has an end section 2 which is connected to the cannula tube 1'. FIG. 1 clearly shows that the end section 2 has a rectilinear design like the cannula tube 1', but is bent to the side relative to the cannula tube 1', which means that the end section defines an angle with the longitudinal axis 9 of the cannula tube, which can be seen in FIG. 3B as angle $\alpha$.

The flow bore of the cannula tube 1' continues in the end section 2 and terminates in a curved section 3 which is connected to the end section 2.

The curved section 3 has, according to FIG. 1, two rounded lengthwise edges with the radius r, which can be seen in FIG. 3B and whose dimensions are reported in Table 1 as a function of various cannula diameters.

The curved section 3 also has on its free end a piercing part 6 which on the front end of the cannula 1 forms and in which a lumen opening 4 disposed in the curved section ends. FIG. 2 clearly shows that the lumen opening 4 is designed in the shape of a lens, however, it terminates in an opening point in the region of a point 7 of the piercing part 6, while the end opposite the point of the opening is rounded.

FIGS. 1 and 2 clearly show that the piercing part 6 is part of the hook-shaped curved section 3, which is connected to the end section 2.

The lumen opening 4 is disposed in the concave side of the curved section 3 and has an rear edge 5 directed inward in the curved section 3 near the end section 2. The lumen opening 4 tangentially ground in the concave shape of the curved section 3 forms on its rear edge 5 a sharply inward directed cutter because of the shape of the end section 2, which cutter contributes decisively to the advantages mentioned in the introduction of the cannula according to the invention.

In the preferred embodiment of the cannula 1 according to the invention depicted in FIGS. 1 and 2, the piercing part 6 has a lancet-shaped point 7 with a beveled ground surface 8. FIG. 1 clearly shows that the point 7 lies in an imaginary cannula tube longitudinal line 9' or is in line with it, whereby the longitudinal line 9' represents the extension of the longitudinal axis 9 of the cannula tube.

FIG. 2 shows that the lancet-shaped point of the depicted embodiment of the cannula 1 is formed by walls 10, 11 of the lumen opening 4.

FIG. 3B illustrates (and FIG. A reports, by way of example, a few preferred sets of dimensions) for the design parameters a (length of the curved section 3), b (length of the end section 2), c (length of the piercing part 6), $\alpha$ (angle between the cannula tube 1' and the end section 2) as well as r (radius of curvature of the lengthwise edges of the curved section 3), all as a function of the cannula diameter d. However, the dimensions in FIG. 3A represent examples only for cannulae with diameters d from 0.6 through 1.5 cm, which yield the preferred measurements contained in the table for the previously mentioned design parameters. However, other cannula diameters are also conceivable with the corresponding, particularly preferred design parameters.

Based on the previously described design of the cannula 1 according to the invention, this cannula is particularly well-suited for piercing natural and synthetic walls since the cutting of plugs from the material to be perforated is avoided.

TABLE 1

| GROUND PORTION | | | |
|---|---|---|---|
| $\alpha = 6°$ $c = \frac{1}{4}$ to $\frac{1}{2} a$ Cannulea d | a | b | r |
| 0.6 | 2.5 | 2.0 | 3.75 |
| 0.7 | 3.0 | 2.0 | 4.50 |
| 0.8 | 3.4 | 2.5 | 5.10 |
| 0.9 | 3.9 | 2.5 | 5.80 |
| 1.0 | 4.3 | 3.0 | 6.40 |
| 1.1 | 4.8 | 3.0 | 7.20 |
| 1.2 | 5.2 | 3.0 | 7.80 |
| 1.5 | 6.5 | 3.0 | 9.75 |

What is claimed is:

1. A cannula comprising:
    a cannula tube having a lumen therethrough, said cannula tube having an upper section at least a portion of which lies on a longitudinal axis of the cannula tube, an end section connected with the upper section and laterally disposed at an acute angle to the longitudinal axis of the cannula tube, and a hook-shaped curved section connected with the end section, the curved section terminating in a piercing part with a lumen opening therein, the lumen opening being tangentially ground into a concave side of the curved section and having, near the end section, a rear edge directed inwardly into the curved section.

2. The cannula according to claim 1, wherein the piercing part has a lancet-shaped point with a beveled ground surface.

3. The cannula according to claim 2, wherein the point lies in an imaginary longitudinal line of the cannula tube which is an extension of the longitudinal axis of the upper section of the cannula tube.

4. The cannula according to claim 1 wherein the acute angle equals 6 degrees.

5. The cannula according to claim 1, wherein the piercing part has a length which equals $\frac{1}{4}$ to $\frac{1}{2}$ the length of the curved section.

6. The cannula according to claim 1, wherein the upper section of the cannula tube is straight.

7. The cannula according to claim 1, wherein the upper section of the cannula tube is bent at a 90°-angle.

8. The cannula according to claim 1, wherein the end section is straight.

9. The cannula according to claim 1, wherein the cannula tube is rigid.

* * * * *